United States Patent
Chan

(10) Patent No.: US 10,610,572 B2
(45) Date of Patent: Apr. 7, 2020

(54) COMPOSITIONS IN THE FORM OF AN INJECTABLE AQUEOUS SOLUTION INCLUDING AT LEAST HUMAN INSULIN A21G AND A GLUCAGON SUPPRESSOR WITH PRANDIAL ACTION

(71) Applicant: ADOCIA, Lyons (FR)

(72) Inventor: You-Ping Chan, Ternay (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 16/048,007

(22) Filed: Jul. 27, 2018

(65) Prior Publication Data

US 2019/0054149 A1   Feb. 21, 2019

(30) Foreign Application Priority Data

Jul. 27, 2017 (FR) .................................. 17 57172
Jul. 28, 2017 (FR) .................................. 17 57184
Jun. 14, 2018 (FR) .................................. 18 55250

(51) Int. Cl.

| | | |
|---|---|---|
| *A61K 38/22* | (2006.01) | |
| *A61K 38/28* | (2006.01) | |
| *A61K 9/00* | (2006.01) | |
| *A61K 47/02* | (2006.01) | |
| *A61K 9/08* | (2006.01) | |
| *C07K 14/62* | (2006.01) | |
| *A61K 45/06* | (2006.01) | |
| *A61K 38/26* | (2006.01) | |
| *A61K 33/30* | (2006.01) | |
| *A61P 3/08* | (2006.01) | |
| *A61K 38/17* | (2006.01) | |
| *A61K 47/10* | (2017.01) | |
| *A61K 47/20* | (2006.01) | |
| *A61P 5/48* | (2006.01) | |
| *A61P 3/10* | (2006.01) | |
| *A61K 47/12* | (2006.01) | |

(52) U.S. Cl.
CPC ............ *A61K 38/28* (2013.01); *A61K 9/0019* (2013.01); *A61K 9/08* (2013.01); *A61K 33/30* (2013.01); *A61K 38/17* (2013.01); *A61K 38/22* (2013.01); *A61K 38/26* (2013.01); *A61K 45/06* (2013.01); *A61K 47/02* (2013.01); *A61K 47/10* (2013.01); *A61K 47/20* (2013.01); *A61P 3/08* (2018.01); *C07K 14/62* (2013.01); *A61K 47/12* (2013.01); *A61P 3/10* (2018.01); *A61P 5/48* (2018.01)

(58) Field of Classification Search
CPC ...... A61K 38/22; A61K 38/28; C07K 14/575; C07K 14/62
See application file for complete search history.

(56) References Cited

U.S. PATENT DOCUMENTS

| | | |
|---|---|---|
| 5,008,241 A | 4/1991 | Markussen et al. |
| 5,124,314 A | 6/1992 | Cooper |
| 5,234,906 A | 8/1993 | Young et al. |
| 5,686,411 A | 11/1997 | Gaeta et al. |
| 6,114,304 A | 9/2000 | Kolterman et al. |
| 6,410,511 B2 | 6/2002 | L'Italien et al. |
| 7,312,196 B2 | 12/2007 | L'Italien et al. |
| 2004/0023871 A1 | 2/2004 | Hiles et al. |
| 2009/0192075 A1 | 7/2009 | Steiner |
| 2010/0222251 A1 | 9/2010 | Schlein |
| 2015/0174209 A1 | 6/2015 | Chiquette et al. |
| 2016/0001002 A1 | 1/2016 | Yodfat et al. |
| 2016/0271226 A1* | 9/2016 | Sahib .................... A61K 38/28 |

FOREIGN PATENT DOCUMENTS

| | | |
|---|---|---|
| EP | 0 196 224 B1 | 8/1989 |
| EP | 2 060 268 A1 | 5/2009 |
| EP | 1 996 224 B1 | 11/2012 |
| WO | 01/04156 A1 | 1/2001 |
| WO | 2007/104786 A1 | 9/2007 |
| WO | 2007/135118 A1 | 11/2007 |
| WO | 2013/067022 A1 | 5/2013 |

OTHER PUBLICATIONS

Gerich, John E. "Control of glycaemia." Ballière's Clinical Endocrinology and Metabolism, vol. 7, p. 551-586, 1993.
Schmitz, Ole, et. al. "Amylin Agonists: A Novel Approach in the Treatment of Diabetes." Diabetes, vol. 53, Supplement 3, p. S233-S238, 2004.

(Continued)

*Primary Examiner* — Jeffrey E. Russel
(74) *Attorney, Agent, or Firm* — Oliff PLC

(57) ABSTRACT

A composition in the form of an injectable aqueous solution, with pH from 3.5 to 4.4, including at least human insulin A21G and at least one glucagon suppressor with prandial action. In an embodiment, the glucagon suppressor with prandial action is selected from an amylin analog or an amylin receptor agonist or a GLP-1 analog or a GLP-1 receptor agonist (GLP-1 RA). In an embodiment, the glucagon suppressor with prandial action is an amylin analog or an amylin receptor agonist. In an embodiment, the glucagon suppressor peptide with prandial action is pramlintide. Also, a method for obtaining human insulin A21G, includes at least one step of reacting human insulin A21G, B31R, B32R (insulin glargine) with rat carboxypeptidase B at an insulin/carboxypeptidase ratio from 500 to 2000, at a pH from 7.5 to 8.5 and a temperature from 20 to 30° C. for 10 to 20 hours.

20 Claims, 2 Drawing Sheets

(56) References Cited

OTHER PUBLICATIONS

Goldsbury, Claire S., et. al. "Polymorphic Fibrillar Assembly of Human Amylin." Journal of Structural Biology, vol. 119, p. 17-27, 1997.
Walsh, Gary. "Therapeutic insulins and their large-scale manufacture." Applied Microbiology Biotechnology, vol. 67, p. 151-159, 2005.
Kohn, Wayne D., et. al. "pI-shifted insulin analogs with extended in vivo time action and favorable receptor selectivity." Peptides, vol. 28, p. 935-948, 2007.
Naiki, Hironobu, et. al. "Fluorometric Determination of Amyloid Fibrils in Vitro Using the Fluorescent Dye, Thioflavine T1." Analytical Biochemistry, vol. 177, p. 244-249, 1989.
LeVine III, Harry. "Quantification of R-Sheet Amyloid Fibril Structures with Thioflavin T." Methods in Enzymology, vol. 309, p. 274-284, 1999.
Yan, Li-Mei, et. al. "Design of a mimic of nonamyloidogenic and bioactive human islet amyloid polypeptide (IAPP) as nanomolar affinity inhibitor of IAPP cytotoxic fibrillogenesis." PNAS. vol. 103, No. 7, 2046-2051, 2006.
Apidra. "Annex 1—Summary of Product Characteristics."
Subramanian, G., et. al. "Structure of Complexes of Cationic Lipids and Poly(Glutamic Acid) Polypeptides: A Pinched Lamellar Phase" J. Am. Chem. Society, vol. 122, p. 26-34, 2000.
Markussen, J., et. al. "Soluble, prolonged-acting insulin derivatives. III. Degree of protraction, crystallizability and chemical stability of insulins substituted in positions A21, B13, B23, B27 and B30." Protein Engineering, vol. 2, No. 2, p. 157-166, 1988.

\* cited by examiner

COMPOSITIONS IN THE FORM OF AN INJECTABLE AQUEOUS SOLUTION INCLUDING AT LEAST HUMAN INSULIN A21G AND A GLUCAGON SUPPRESSOR WITH PRANDIAL ACTION

The invention relates to the therapies by injection of a composition including at least human insulin A21G, with prandial action, and a glucagon suppressor, in particular with prandial action, for treating diabetes and for allowing the improvement of the control of postprandial hyperglycemia.

Type 1 diabetes is an autoimmune disease leading to the destruction of the beta cells of the pancreas. These cells are known to produce insulin, the main role of which is to regulate the use of glucose in the peripheral tissues (Gerich 1993 Control of glycaemia). Consequently, type 1 diabetes patients suffer from chronic hyperglycemia and have to self-administer exogenous insulin in order to limit this hyperglycemia. Insulin therapy has drastically changed the life expectancy of these patients.

To date, type 1 diabetes patients use two types of insulin, short-acting prandial insulins for controlling glycemia at meal time, and long-acting basal insulins for controlling glycemia throughout the day and night. Several types of short-acting insulins exist, which are characterized by their onset of action. For example, human insulin, referred to as regular insulin, has a delayed action in comparison to the so-called rapid insulin analogs such as insulin lispro (Humalog®, ELI LILLY) or insulin aspart (Novorapid®, NOVO NORDISK). Thus, human insulin has to be administered on average 30 minutes before the meal, while the insulin analogs can be administered 15 minutes before the meal or at meal time. In addition, insulin analogs are considered to lead to a better control of post-prandial glycemia than human insulin, which explains why a very large majority of patients in Europe and in the United States today use rapid insulin analogs whose action is shorter than that of human insulin.

However, the control of glycemia ensured by these exogenous prandial insulins after consumption of a meal is not optimal, even in the case of rapid insulin analogs. This is in part associated with the fact that these patients, in contrast to healthy persons, produce glucagon after consumption of a meal, which leads to the removal of some of the glucose stored in the liver. This glucose production mediated by glucagon worsens the post-prandial hyperglycemia problem of these patients and leads to excessive use of insulin.

This problem of regulation of post-prandial glycemia is rather similar for type 2 diabetes patients treated with insulin, in cases in which their disease has resulted in a very significant loss of their ability to produce insulin and amylin.

It has been demonstrated that glucagon suppressors, in particular peptides and/or hormones, are capable of inhibiting glucagon production after consumption of a meal, which leads to a significant improvement of the control of post-prandial glycemia. For example, amylin, a hormone produced by the beta cells of the pancreas, whose production is also deficient in type 1 diabetes patients, plays a key role in the regulation of the post-prandial glycemia. Amylin, also known under the name of "islet amyloid polypeptide" or IAPP, is a 37 amino acid peptide which is co-stored and co-secreted with the insulin (Schmitz 2004 Amylin Agonists). This peptide is described as a blocker of glucagon production by the alpha cells of the pancreas. Thus, insulin and amylin have complementary and synergetic roles, since insulin enables to reduce the glucose concentration in the blood, while amylin enables to reduce the entry of endogenous glucose into the blood by inhibiting the production or secretion of endogenous glucagon.

However, human amylin has properties that are not compatible with the pharmaceutical requirements in terms of solubility and stability (Goldsbury C S, Cooper G J, Goldie K N, Muller S A, Saafi E L, Gruijters W T, Misur M P, Engel A, Aebi U, Kistler J: Polymorphic fibrillar assembly of human amylin. J Struct Biol 119:17-27, 1997). Amylin is known to form amyloid fibers leading to the formation of water-insoluble plaque. Consequently, it has been necessary to develop an analog to solve these solubility problems.

The company Amylin has developed an analog of amylin, pramlintide, to compensate the lack of physical stability of human amylin. This product, marketed under the name of Symlin®, was approved in 2005 by the FDA for the treatment of type 1 and type 2 diabetes, as a complement to insulin therapy. It must be administered by the subcutaneous route three times daily, in the hour preceding the meal, in order to improve the control of post-prandial glycemia, taking into consideration its relatively short half-life of several hours. This peptide is formulated at pH 4.0 and it has been described to undergo fibrillation when the pH of the solution is higher than 5.5. Variants of analogs are described in the U.S. Pat. No. 5,686,411.

The amylin analogs or the amylin receptor agonists referred to as "prandial" or "short-acting" reproduce the effects of amylin while having a longer half-life. These derivatives of amylin which enable to control glycemia at meal time can have a half-life of less than 8 h. This half-life is the apparent half-life of elimination after subcutaneous injection in humans. The half-life of these amylin analogs or amylin receptor agonists can be less than 5 hours, in particular less than 4 hours, and even less than 3 hours.

However, the compositions including amylin or an amylin analog and in particular pramlintide can induce certain adverse effects in the patients. In particular, these compositions can cause nausea in patients.

GLP-1, another physiological peptide, is also described to play a similar role to that of amylin in terms of suppression of glucagon secretion after consumption of a meal. GLP-1 is also known for its role as an insulin secretagogue and is thus particularly effective when used as a complement to insulin, in particular in type 2 diabetes patients. These actions are glucose-dependent, which minimizes the risk of hypoglycemia. GLP-1 RA have been approved so far only for type 2 diabetes patients.

Likewise, human GLP-1 cannot be used as a therapeutic treatment due to its extremely short half-life. Various GLP-1 derivatives, GLP-1 receptor agonists, referred to as GLP-1 RA, or GLP-1 analogs reproduce the effects of GLP-1, while having a longer half-life. These GLP-1 derivatives can be distributed into three groups depending on their respective half-lives: those with short action, or prandial, for controlling glycemia at meal time (half-life of less than 8 h), those with action for a day, which cover the needs in the course of the day (half-life of more than 8 h, or 10 h), and those with action for a week, which cover the needs during the week (half-life of more than 48 h). With regard to GLP-1 RA with prandial action, the two peptides approved to date are exenatide (Byetta®, ASTRA-ZENECA, two administrations daily) and lixisenatide (Lyxumia®, SANOFI, one administration daily). These two GLP-1 RA are formulated at a pH close to 4 and have to be administered in the hour preceding the meal, like pramlintide.

For insulin-dependent patients, one of the main difficulties in using these different short-acting glucagon suppressor compounds is associated with the number of additional injections, which can range from 1 to 3 injections daily in addition to the 2 to 4 injections of insulin. Thus, it is crucial to be able to combine in a solution a prandial insulin with a glucagon suppressor with prandial action, in order to enable the use of these compounds complementary to insulin without complicating the treatment for the patients. In addition, it would be possible to mimic the physiology more finely, since both these hormones are secreted in response to a meal, in order to improve the control of post-prandial glycemia, in particular a better control post-prandial hyperglycemia, and thus to better treat the diabetes.

But prandial insulins and these peptides of interest are not compatible in an aqueous solution. Indeed, the prandial insulins have an optimal chemical stability at a pH close to 7, while the derivatives of amylin or of GLP-1 are physically and chemically unstable at a pH close to physiological pH.

This difficulty has led to the design of pumps containing two reservoirs for keeping the prandial insulin separate from the amylin derivative. The US patent US2016/001002 from the company ROCHE describes such a pump, in order to enable the co-administration of amylin and of a prandial insulin using a single medical device. However, it would be preferable to be able to mix these hormones in an aqueous solution, in order to use existing medical devices that are simpler and/or that have a reduced risk of failure.

Another solution to this problem of mixing these hormones in an aqueous solution consists in replacing the water with an organic solvent. The patent application WO2013067022 from the company XERIS describes compositions which include amylin and insulin in solution in an organic solvent. However, the use of an organic solvent such as DMSO raises safety questions for the patient in the treatment of a chronic disease such as diabetes. Moreover, the organic solvents can be problematic with regard to the injection devices, in particular as they dissolve some of certain components of said injection devices. Therefore, it is desirable to develop these combinations in the form of an aqueous solution.

The problem of stability in an aqueous solution has also been circumvented by preparing mixtures in the solid state. The patent application EP2060268 from NOVO NORDISK describes formulations of insulin and pramlintide in the form of an atomized powder for nasal application. However, the preferred and most used route of administration to date is the subcutaneous route which requires the obtention of ready-to-use aqueous solutions.

Another approach consists in combining a prandial insulin with an amylin derivative at the pH at which this amylin derivative is physically stable. The patent application US20090192075 from the company Biodel describes a liquid composition including human insulin, pramlintide and a zinc chelator at pH 4.0. This application describes a rapid action of the human insulin due to the presence of a zinc chelating agent. However, human insulin is known for not being chemically stable at acidic pH, this technique would not satisfy the criteria of the EP and/or US Pharmacopoeia.

An alternative approach consists in modifying the structure of the prandial insulins to improve their stability at acidic pH. The application WO2007104786 exemplifies compositions including the rapid insulin analogs A21G, B28D, desB30 and A21G, B28E, desB30 which are soluble at acidic pH.

The application WO2007104786 also presents rapid insulin compositions, in particular B28D (insulin aspart) at neutral pH and in the presence of a surfactant, and in particular of a glycerophosphate derivative, more particularly dimyristoyl glycerophosphoglycerol (DMPG), leading to stabilities measured by ThT much greater than the stabilities of compositions of rapid insulin analogs A21G, B28D, desB30 and A21G, B28E, desB30 at acidic pH.

The compositions of the prior art including a prandial insulin and pramlintide in combination most of the time describe the different types of prandial insulins; however, their examples relate to compositions including so-called rapid prandial insulin analogs, the latter being considered more effective than human insulin.

Surprisingly, the applicant has demonstrated that a composition containing human insulin A21G, referred to as "regular," that is to say an insulin differing from human insulin only in the replacement of the asparagine residue in position 21 on the A chain by a glycine residue, less rapid than the so-called "rapid" insulin analogs, in combination with a glucagon suppressor with prandial action at a pH ranging from 3.5 to 4.4 in an aqueous solution enables to obtain a better control of post-prandial glycemia than with a so-called rapid prandial insulin analog.

In addition, the applicant has demonstrated surprisingly that said composition containing human insulin A21G, in combination with a glucagon suppressor with prandial action at a pH ranging from 3.5 to 4.4 in an aqueous solution exhibits a physical and chemical stability compatible with the pharmaceutical requirements and greater than the solutions proposed in the prior art.

The obtention of a composition in the form of an injectable aqueous solution exhibiting a better control of post-prandial hyperglycemia and improved physical and chemical stability properties in comparison to those described in the prior art is remarkable, since it is well known to the person skilled in the art that, in the case of combinations, the pharmacokinetics of the products in combinations and the physical and chemical stability properties are very difficult to predict.

Moreover, also sought is a composition which enables to decrease and even eliminate all or some of the adverse effects that can be generated by the active substances.

The invention relates to a composition in the form of an injectable aqueous solution, the pH of which is from 3.5 to 4.4, including at least the so-called regular human insulin A21G and at least one glucagon suppressor with prandial action.

According to an embodiment, the glucagon suppressor with prandial action is an amylin analog or an amylin receptor agonist, a GLP-1 analog or a GLP-1 receptor agonist, also referred to as GLP-1 RA.

The applicant has observed that the formulation according to the invention at a pH from 3.5 to 4.4 has pharmacokinetic properties compatible with use at meal times and enables a better control of post-prandial glycemia.

In addition, the applicant has shown that these formulations lead to a slowing of the absorption of pramlintide. This is characterized in particular by a pramlintide plasma peak ($t_{max}$) which is significantly delayed and/or by an early plasma exposure to pramlintide ($AUC_{0\text{-}30\ min}$) which is significantly decreased in comparison to the administration of pramlintide alone.

This slowing enables to decrease and even eliminate the adverse effects of pramlintide, in particular insofar as nausea is concerned.

The invention also relates to the use of a composition in the form of an injectable aqueous solution, the pH of which is from 3.5 to 4.4, including at least human insulin A21G and a glucagon suppressor, in particular with prandial action, to improve the control post-prandial glycemia.

The invention also relates to a composition according to the invention which is intended to be used in a diabetes treatment method, characterized in that it is administered in a bolus before meals.

The invention also relates to a composition according to the invention which is intended to be used in a diabetes treatment method, characterized in that it is administered to improve the control of post-prandial glycemia.

The invention also relates to a composition according to the invention which is intended to be used in a diabetes treatment method, characterized in that it is administered to improve the control of post-prandial glycemia and to decrease the adverse effects of pramlintide.

The invention also relates to a composition according to the invention which is intended to be used in a diabetes treatment method, characterized in that it enables to decrease the food consumption induced by insulin.

According to an embodiment, the decrease in food consumption relates to the period from the injection to 4 hours after the injection.

According to an embodiment, the decrease in food consumption relates to the period from the injection to 3 hours after the injection.

According to an embodiment, the decrease in food consumption relates to the period from the injection to 2 hours after the injection.

According to an embodiment, the decrease in food consumption relates to the period from the injection to 1 hour after the injection.

The invention also relates to stable pharmaceutical compositions including such compositions.

The requirements that enable to obtain an injectable pharmaceutical formulation for diabetes treatment are in particular:
- an aqueous liquid formulation which is physically and chemically stable for at least two weeks or even for one month at 30° C. (multiple uses) and for at least one year or even 2 years at 5° C.,
- a compatibility with the antimicrobial preservatives.

Likewise, the formulations of human insulin A21G with a GLP-1 analog or a GLP-1 receptor agonist, also referred to as GLP-1 RA, for example, exenatide or lixisenatide, at a pH from 3.5 to 4.4, have a physical and chemical stability enabling the development of a liquid formulation which is stable for at least 2 weeks or even one month at 30° C., and for at least one year or even 2 years at 5° C.

With regard to the stability, the conventional method for measuring the stabilities of proteins or peptides consists in measuring the formation of fibrils with the aid of thioflavin T, also referred to as ThT. This method enables to measure, under temperature and stirring conditions enabling an acceleration of the phenomenon, the lag time before the formation of fibrils by measuring the increase in fluorescence. The compositions according to the invention have a lag time before the formation of fibrils that is clearly greater than those described in the literature. The compositions according to the invention exhibit a physical and chemical stability which is much greater than those described in the prior art by using commercial prandial insulins.

In an embodiment, the formulations according to the invention exhibit a lag time measured by ThT equal to at least 8 hours.

In an embodiment, the formulations according to the invention exhibit a lag time measured by ThT equal to at least 10 hours.

In an embodiment, the formulations according to the invention exhibit a lag time measured by ThT equal to at least 15 hours.

In an embodiment, the formulations according to the invention exhibit a lag time measured by ThT equal to at least 20 hours.

In an embodiment, the formulations according to the invention exhibit a lag time measured by ThT equal to at least 25 hours.

In an embodiment, the invention relates to a composition in the form of an injectable aqueous solution, the pH of which is from 3.5 to 4.4, including at least human insulin A21G and an amylin receptor agonist or an amylin analog. According to an embodiment, said amylin receptor agonist or amylin analog is pramlintide.

In an embodiment, the invention relates to a composition in the form of an injectable aqueous solution, the pH of which is from 3.5 to 4.2, including at least human insulin A21G and an amylin receptor agonist or an amylin analog. According to an embodiment, said amylin receptor agonist or amylin analog is pramlintide.

In an embodiment, the invention relates to a composition in the form of an injectable aqueous solution, the pH of which is from 3.8 to 4.2, including at least human insulin A21G and an amylin receptor agonist or an amylin analog. According to an embodiment, said amylin receptor agonist or amylin analog is pramlintide.

In an embodiment, the invention relates to a composition in the form of an injectable aqueous solution, the pH of which is 4.0, including at least human insulin A21G and an amylin receptor agonist or an amylin analog. According to an embodiment, said amylin receptor agonist or amylin analog is pramlintide.

In an embodiment, the invention relates to a composition in the form of an injectable aqueous solution, the pH of which is between 3.5 to 4.4, including at least human insulin A21G and a GLP-1 receptor agonist or a GLP-1 analog. According to an embodiment, said GLP-1 receptor agonist is exenatide. According to another embodiment, said GLP-1 receptor agonist is lixisenatide.

In an embodiment, the invention relates to a composition in the form of an injectable solution, the pH of which is between 3.5 to 4.2, including at least human insulin A21G and a GLP-1 receptor agonist or a GLP-1 analog. According to an embodiment, said GLP-1 receptor agonist is exenatide. According to another embodiment, said GLP-1 receptor agonist is lixisenatide.

In an embodiment, the invention relates to a composition in the form of an injectable aqueous solution, the pH of which is between 3.8 to 4.2, including at least human insulin A21G and a GLP-1 receptor agonist or a GLP-1 analog. According to an embodiment, said GLP-1 receptor agonist is exenatide. According to another embodiment, said GLP-1 receptor agonist is lixisenatide.

In an embodiment, the invention relates to a composition in the form of an injectable aqueous solution, the pH of which is 4.0, including at least human insulin A21G and a GLP-1 receptor agonist or a GLP-1 analog. According to an embodiment, said GLP-1 receptor agonist is exenatide. According to another embodiment, said GLP-1 receptor agonist is lixisenatide.

In an embodiment, the invention relates to a composition in the form of an injectable aqueous solution, the pH of which is from 3.5 to 4.4, including at least human insulin A21G, an amylin receptor agonist or an amylin analog, and a GLP-1 receptor agonist or a GLP-1 analog. According to an embodiment, said GLP-1 receptor agonist is exenatide.

According to another embodiment, said GLP-1 receptor agonist is lixisenatide. According to yet another embodiment, said amylin receptor agonist or amylin analog is pramlintide.

In an embodiment, the invention relates to a composition in the form of an injectable aqueous solution, the pH of which is from 3.5 to 4.2, including at least human insulin A21G, at least one amylin receptor agonist or an amylin analog, and at least one GLP-1 receptor agonist or a GLP-1 analog. According to an embodiment, said GLP-1 receptor agonist is exenatide. According to another embodiment, said GLP-1 receptor agonist is lixisenatide. According to yet another embodiment, said amylin receptor agonist or amylin analog is pramlintide.

In an embodiment, the invention relates to a composition in the form of an injectable aqueous solution, the pH of which is from 3.8 to 4.2, including at least human insulin A21G, at least one amylin receptor agonist or an amylin analog, and at least one GLP-1 receptor agonist or a GLP-1 analog. According to an embodiment, said GLP-1 receptor agonist is exenatide. According to another embodiment, said GLP-1 receptor agonist is lixisenatide. According to yet another embodiment, said amylin receptor agonist or amylin analog is pramlintide.

In an embodiment, the invention relates to a composition in the form of an injectable aqueous solution, the pH of which is 4.0, including at least human insulin A21G, at least one amylin receptor agonist or an amylin analog, and at least one GLP-1 receptor agonist or a GLP-1 analog. According to an embodiment, said GLP-1 receptor agonist is exenatide. According to another embodiment, said GLP-1 receptor agonist is lixisenatide. According to yet another embodiment, said amylin receptor agonist or amylin analog is pramlintide.

It is particularly advantageous to combine, in an aqueous solution, human insulin A21G with an amylin analog, an amylin receptor agonist or GLP-1 and with a GLP-1 analog or a GLP-1 receptor agonist, since this so-called "triple" combination enables in particular to potentiate the effects of each hormone and reduce the doses of each of them.

The compositions in the form of an injectable aqueous solution according to the invention are clear solutions. "Clear solution" is understood to mean compositions which satisfy the criteria described in the American and European pharmacopoeias concerning the injectable solutions. In the US pharmacopoeia, the solutions are defined in part <1151> referring to the injection (<1>) (referring to <788> according to USP 35 and specified in <788> according to USP 35 and in <787>, <788> and <790> USP 38 (from Aug. 1, 2014), according to USP 38). In the European pharmacopoeia, the injectable solutions have to meet the criteria given in sections 2.9.19 and 2.9.20.

In the present application, as mentioned, amylin refers to the compounds described in the U.S. Pat. Nos. 5,124,314 and 5,234,906. When the term "analog" is used, it refers to a peptide or a protein in which one or more constitutive amino acid residues of the primary sequence have been substituted by other amino acid residues and/or in which one or more constitutive amino acid residues have been eliminated and/or in which one or more constitutive amino acid residues have been added. The percentage of homology that is accepted for the present definition of an analog is 50%. In the case of amylin, an analog can be, for example, derived from the primary amino acid sequence of amylin by substituting one or more natural or non-natural or peptidomimetic amino acids.

Exenatide and lixisenatide, which are described in the applications US2004/0023871 and WO0104156, respectively, are generally considered to be GLP-1 receptor agonists. In an embodiment, the glucagon suppressor with prandial action is pramlintide (Symlin®) marketed by the company ASTRAZENECA AB.

In an embodiment, the GLP-1, GLP-1 analogs, or GLP-1 RA are referred to as "short-acting" or "prandial." "Short-acting" or "prandial" is understood to mean GLP-1, GLP-1 analogs, or GLP-1 RA of which the apparent half-life of elimination after subcutaneous injection in humans is less than 8 hours, in particular less than 5 hours, preferably less than 4 hours or else less than 3 hours, such as, for example, exenatide or lixisenatide.

In an embodiment, the GLP-1, the GLP-1 analogs, or the GLP-1 RA are selected from the group consisting of exenatide (Byetta®, ASTRA-ZENECA), lixisenatide (Lyxumia®, SANOFI), the analogs or derivatives thereof and pharmaceutically acceptable salts thereof.

In an embodiment, the GLP-1, the GLP-1 analog, or GLP-1 RA is exenatide or Byetta®, analogs or derivatives thereof and pharmaceutically acceptable salts thereof.

In an embodiment, GLP-1, GLP-1 analog, or GLP-1 RA is lixisenatide or Lyxumia®, analogs or derivatives thereof and pharmaceutically acceptable salts thereof.

In an embodiment, the concentration of human insulin A21G is from 240 to 3000 μM or from 40 to 500 U/mL.

In an embodiment, the concentration of human insulin A21G is 600 μM or 100 U/mL.

In an embodiment, the concentration of human insulin A21G is 1200 μM or 200 U/mL.

In an embodiment, the concentration of human insulin A21G is 1800 μM or 300 U/mL.

In an embodiment, the concentration of human insulin A21G is 2400 μM or 400 U/mL.

In an embodiment, the concentration of human insulin A21G is 3000 μM or 500 U/mL.

In the present application, 100 U/mL of human insulin A21G corresponds to 3.5 mg/mL.

In an embodiment, the concentration of pramlintide is from 0.32 to 5 mg/mL.

In an embodiment, the concentration of pramlintide is from 0.4 to 3 mg/mL.

In an embodiment, the concentration of pramlintide is from 0.5 to 2 mg/mL.

In an embodiment, the concentration of pramlintide is from 0.5 to 1.5 mg/mL.

In an embodiment, the concentration of pramlintide is from 0.6 to 1 mg/mL.

In an embodiment, the concentration of pramlintide is 1.0 mg/mL.

In an embodiment, the concentration of pramlintide is 0.6 mg/mL.

In an embodiment, the concentration of exenatide is from 10 to 1000 μg/mL.

In an embodiment, the concentration of exenatide is from 10 to 500 μg/mL.

In an embodiment, the concentration of exenatide is from 20 to 400 μg/mL.

In an embodiment, the concentration of exenatide is from 20 to 300 μg/mL.

In an embodiment, the concentration of exenatide is from 30 to 300 μg/mL. In an embodiment, the concentration of exenatide is from 30 to 150 μg/mL.

In an embodiment, the concentration of exenatide is from 40 to 150 μg/mL.

In an embodiment, the concentration of exenatide is from 40 to 80 μg/mL.

In an embodiment, the concentration of exenatide is 50 μg/mL.

In an embodiment, the concentration of lixisenatide is from 20 to 1000 μg/mL.

In an embodiment, the concentration of lixisenatide is from 20 to 800 μg/mL.

In an embodiment, the concentration of lixisenatide is from 40 to 600 μg/mL.

In an embodiment, the concentration of lixisenatide is from 60 to 600 μg/mL.

In an embodiment, the concentration of lixisenatide is from 60 to 300 μg/mL.

In an embodiment, the concentration of lixisenatide is from 80 to 300 μg/mL.

In an embodiment, the concentration of lixisenatide is from 80 to 160 μg/mL.

In an embodiment, the concentration of lixisenatide is 100 μg/mL.

In an embodiment, the concentration of exenatide, analogs or derivatives thereof and pharmaceutically acceptable salts thereof is in a range from 0.01 to 1.0 mg per 100 U of insulin.

In an embodiment, the concentration of exenatide, analogs or derivatives thereof and pharmaceutically acceptable salts thereof is from 0.01 to 0.5 mg per 100 U of insulin.

In an embodiment, the concentration of exenatide, analogs or derivatives thereof and pharmaceutically acceptable salts thereof is from 0.02 to 0.4 mg per 100 U of insulin.

In an embodiment, the concentration of exenatide, analogs or derivatives thereof and pharmaceutically acceptable salts thereof is from 0.03 to 0.3 mg per 100 U of insulin.

In an embodiment, the concentration of exenatide, analogs or derivatives thereof and pharmaceutically acceptable salts thereof is from 0.03 to 0.2 mg per 100 U of insulin.

In an embodiment, the concentration of exenatide, analogs or derivatives thereof and pharmaceutically acceptable salts thereof is from 0.03 to 0.15 mg per 100 U of insulin.

In an embodiment, the concentration of exenatide, analogs or derivatives thereof and pharmaceutically acceptable salts thereof is from 0.05 mg per 100 U of insulin.

In an embodiment, the concentration of lixisenatide, analogs or derivatives thereof and pharmaceutically acceptable salts thereof is in a range from 0.01 to 1 mg per 100 U of insulin.

In an embodiment, the concentration of lixisenatide, analogs or derivatives thereof and pharmaceutically acceptable salts thereof is from 0.01 to 0.5 mg per 100 U of insulin.

In an embodiment, the concentration of lixisenatide, analogs or derivatives thereof and pharmaceutically acceptable salts thereof is from 0.02 to 0.4 mg per 100 U of insulin.

In an embodiment, the concentration of lixisenatide, analogs or derivatives thereof and pharmaceutically acceptable salts thereof is from 0.03 to 0.3 mg per 100 U of insulin.

In an embodiment, the concentration of lixisenatide, analogs or derivatives thereof and pharmaceutically acceptable salts thereof is from 0.04 to 0.2 mg per 100 U of insulin.

In an embodiment, the concentration of lixisenatide, analogs or derivatives thereof and pharmaceutically acceptable salts thereof is from 0.04 to 0.15 mg per 100 U of insulin.

In an embodiment, the concentration of lixisenatide, analogs or derivatives thereof and pharmaceutically acceptable salts thereof is 0.1 mg per 100 U of insulin.

In an embodiment, the compositions according to the invention are prepared by mixing solutions of amylin analogs or of amylin receptor agonists, and solutions of GLP-1, of GLP-1 analog or of GLP-1 receptor agonist RA in ratios by volume in a range from 10/90 to 90/10.

In an embodiment, the compositions according to the invention moreover include zinc salts at a concentration from 0 to 800 μM per 100 U of insulin.

In an embodiment, the compositions according to the invention moreover include zinc salts at a concentration from 0 to 500 μM per 100 U of insulin.

In an embodiment, the compositions according to the invention moreover include zinc salts at a concentration from 100 to 500 μM per 100 U of insulin.

In an embodiment, the compositions according to the invention moreover include zinc salts at a concentration from 200 to 400 μM per 100 U of insulin.

In an embodiment, the compositions according to the invention moreover include zinc salts at a concentration of 300 μM per 100 U of insulin.

In an embodiment, the compositions according to the invention moreover include buffers.

In an embodiment, the compositions according the invention include a buffer selected from the group consisting of a sodium acetate buffer and Tris.

In an embodiment, the compositions according the invention moreover include preservatives.

In an embodiment, the preservatives are selected from the group consisting of m-cresol and phenol, alone or in a mixture.

In an embodiment, the concentration of preservatives is from 10 to 50 mM.

In an embodiment, the concentration of preservatives is from 10 to 40 mM.

In an embodiment, the compositions according to the invention moreover include a surfactant.

In an embodiment, the surfactant is selected from the group consisting of Poloxamer 188, Tween® 20, also referred to as Polysorbate 20, and Tween® 80, also referred to as Polysorbate 80.

In an embodiment, the Tween® 20 concentration varies from 5 to 50 μg/mL.

In an embodiment, the Tween® 20 concentration varies from 5 to 25 μg/mL.

In an embodiment, the Tween® 20 concentration is 10 μM.

The compositions according to the invention can moreover include additives such as tonicity agents.

In an embodiment, the tonicity agents are selected from the group consisting of glycerol, sodium chloride, mannitol and glycine.

In an embodiment, the compositions according to the invention moreover include an antioxidant.

In an embodiment, the antioxidant is methionine.

In an embodiment, the pharmaceutical composition moreover includes at least one absorption promoter selected from the absorption promoters, the diffusion promoters or the vasodilating agents, alone or in a mixture.

The absorption promoters include, but are not limited to, the surfactants, for example, the biliary salts, the fatty acid salts or the phospholipids; the nicotinic agents such as nicotinamides, the nicotinic acids, niacin, niacinamide, vitamin B3 and salts thereof; the pancreatic trypsin inhibitors; the magnesium salts; the polyunsaturated fatty acids; phosphatidylcholine didecanoyl; the aminopolycarboxylates; tolmetin; sodium caprate; salicylic acid; oleic acid; linoleic acid; eicosapentaenoic acid (EPA); docosahexaenoic acid (DHA); benzylic acid; nitrogen monoxide donors, for example, 3-(2-hydroxy-1-(1-methylethyl)-2-nitrosohydrazino)-1-propanamine, N-ethyl-2-(1-ethylhydroxy-2-1-nitrosohydrazino)ethanamine, or S-nitroso-N-acetylpenicillamine; the biliary acids, glycine in its conjugated form with a biliary acid; sodium ascorbate, potassium ascorbate; sodium salicylate, potassium salicylate, acetylsalicylic acid, salicylosalicylic acid, aluminum acetylsalicylate, choline salicylate, salicylamide, lysine acetylsalicylate; exalamide; diflunisal; ethenzamide; EDTA; alone or in a mixture.

In an embodiment, the pharmaceutical composition moreover includes at least one diffusion promoter. Examples of diffusion promoters include, but are not limited to, the glycosaminoglycanases, for example, hyaluronidase.

In an embodiment, the pharmaceutical composition moreover includes at least one vasodilating agent.

In an embodiment, the pharmaceutical composition moreover includes at least one vasodilating agent inducing hyperpolarization by blocking the calcium ion channels.

In an embodiment, the vasodilating agent inducing hyperpolarization by blocking the calcium ion channels is adenosine, a hyperpolarizing agent derived from the endothelium, a phosphodiesterase type 5 (PDES) inhibitor, a potassium channel opening agent or any combination of these agents.

In an embodiment, the pharmaceutical composition moreover includes at least one vasodilating agent with mediation by AMPc.

In an embodiment, the pharmaceutical composition moreover includes at least one vasodilating agent with mediation by GMPc.

In an embodiment, the pharmaceutical composition moreover comprises at least one vasodilating agent selected from the group including the vasodilating agents which act by inducing hyperpolarization by blocking the calcium ion channels, the vasodilating agents with mediation by AMPc, and the vasodilating agents with mediation by GMPc.

The at least one vasodilating agent is selected from the group including the nitrogen monoxide donors, for example, nitroglycerine, isosorbide dinitrate, isosorbide mononitrate, amyl nitrate, erythrityl, tetranitrate, and nitroprussiate; prostacyclin and analogs thereof, for example, sodium epoprostenol, iloprost, epoprostenol, treprostinil or selexipag; histamine, 2-methylhistamine, 4-methylhistamine; 2-(2-pyridyl)ethylamine, 2-(2-thiazolyl)ethylamine; papaverine, papaverine hydrochloride; minoxidil; dipyridamole; hydralazine; adenosine, adenosine triphosphate; uridine trisphosphate; GPLC; L-carnitine; arginine; prostaglandin D2; the potassium salts; and, in some cases, the α1 and α2 receptor antagonists, for example, prazosin, phenoxybenzamine, phentolamine, dibenamine, moxisylyte hydrochloride and tolazoline), betazole, dimaprit; the β2 receptor agonists, for example, isoproterenol, dobutamine, albuterol, terbutaline, aminophylline, theophylline, caffeine; alprostadil, ambrisentan; cabergoline; diazoxide; dihydralazine mesilate; diltiazem hydrochloride; enoximone; flunarizine hydrochloride; *Ginkgo biloba* extract; levosimendan; molsidomine; naftidrofuryl acid oxalate; nicorandil; pentoxifylline; phenoxybenzamine chloride; piribedil base; piribedil mesilate; regadenoson monohydrate; riociguat; sildenafil citrate, tadalafil, trihydrated vardenafil hydrochloride; trimetazidine hydrochloride; trinitrin; verapamil hydrochloride; endothelin receptor antagonists, for example, avanafil and bosentran monohydrate; and the calcium channel inhibitors, for example amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, prandipine; alone or in a mixture.

In an embodiment, the composition according to the invention contains 3.5 mg/mL to 10.5 mg/mL of human insulin A21G, 0.6 mg/mL to 3 mg/mL of pramlintide, 25 mM of m-cresol, 184 mM of glycerol at a pH of 4.0. This composition can moreover contain from 300 to 900 μM of zinc. This composition can moreover include polysorbate 20, in particular from 8 to 10 μM, and most particularly 8 μM.

In an embodiment, the composition according to the invention contains 3.5 mg/mL of human insulin A21G, 0.6 to 1 mg/mL of pramlintide, 25 to 30 mM of m-cresol, 150 to 200 mM of glycerol, at a pH of 4.0. This composition can moreover contain 300 μM of zinc. This composition can moreover include polysorbate 20, in particular from 8 to 10 μM, and most particularly 8 μM.

In an embodiment, the composition according to the invention contains 3.5 mg/mL of human insulin A21G, 0.6 mg/mL of pramlintide, 25 mM of m-cresol, 184 mM of glycerol, at a pH of 4.0. This composition can moreover contain 300 μM of zinc. This composition can moreover include polysorbate 20, in particular 10 μM.

In an embodiment, the composition according to the invention contains 3.5 mg/mL of human insulin A21G, 0.6 mg/mL of pramlintide, 25 mM of m-cresol, 184 mM of glycerol, at a pH of 4.0. This composition can moreover contain 300 μM of zinc. This composition can moreover include polysorbate 20, in particular 8 μM.

In an embodiment, the composition according to the invention contains 3.5 mg/mL of human insulin A21G, 1.0 mg/mL of pramlintide, 25 mM of m-cresol, 184 mM of glycerol, at a pH of 4.0. This composition can moreover contain 300 μM of zinc. This composition can moreover include polysorbate 20, in particular 8 μM.

In an embodiment, the composition according to the invention contains 7.0 mg/mL of human insulin A21G, from 1.2 to 2.0 mg/mL of pramlintide, 25 mM of m-cresol, 150 to 200 mM of glycerol, at a pH of 4.0. This composition can moreover contain 600 μM of zinc. This composition can moreover include polysorbate 20, in particular from 8 to 10 μM, and most particularly 8 μM.

In an embodiment, the composition according to the invention contains 7.0 mg/mL of human insulin A21G, 1.2 mg/mL of pramlintide, 25 mM of m-cresol, 184 mM of glycerol, at a pH of 4.0. This composition can moreover contain 600 μM of zinc. This composition can moreover include polysorbate 20, in particular 10 μM.

In an embodiment, the composition according to the invention contains 7.0 mg/mL of human insulin A21G, 1.2 mg/mL of pramlintide, 25 mM of m-cresol, 184 mM of glycerol, at a pH of 4.0. This composition can moreover contain 600 μM of zinc. This composition can moreover include polysorbate 20, in particular 8 μM.

In an embodiment, the composition according to the invention contains 7.0 mg/mL of human insulin A21G, 2.0 mg/mL of pramlintide, 25 mM of m-cresol, 184 mM of glycerol, at a pH de 4.0. This composition can moreover contain 600 μM of zinc. This composition can moreover include polysorbate 20, in particular 8 μM.

In an embodiment, the composition according to the invention contains 10.5 mg/mL of human insulin A21G, 1.8 to 3 mg/mL of pramlintide, 25 mM of m-cresol, 150 to 200 mM of glycerol, at a pH of 4.0. This composition can moreover contain 900 μM of zinc. This composition can moreover include polysorbate 20, in particular from 8 to 10 μM, and most particularly 8 μM.

In an embodiment, the composition according to the invention contains 10.5 mg/mL of human insulin A21G, 1.8 mg/mL of pramlintide, 25 mM of m-cresol, 184 mM of glycerol, at a pH of 4.0. This composition can moreover contain 900 µM of zinc. This composition can moreover include polysorbate 20, in particular 10 µM.

In an embodiment, the composition according to the invention contains 10.5 mg/mL of human insulin A21G, 1.8 mg/mL of pramlintide, 25 mM of m-cresol, 184 mM of glycerol, at a pH de 4.0. This composition can moreover contain 900 µM of zinc.

This composition can moreover include polysorbate 20, in particular 8 µM.

In an embodiment, the composition according to the invention contains 10.5 mg/mL of human insulin A21G, 3 mg/mL of pramlintide, 25 mM of m-cresol, 184 mM of glycerol, at a pH of 4.0. This composition can moreover contain 900 µM of zinc. This composition can moreover include polysorbate 20, in particular 8 µM.

The compositions according to the invention can moreover include all the excipients in compliance with the Pharmacopoeias, in particular the EP and/or US Pharmacopoeias, and compatible with the insulins used at the usual concentrations.

According to an embodiment, the composition can be in solid or lyophilized form. This composition can then be used to reconstitute a solution or a formulation.

The methods of administration considered are the intravenous, subcutaneous, intradermal or intramuscular route.

According to a particular embodiment, the method of administration is the subcutaneous route.

The transdermal, oral, nasal, vaginal, ocular, buccal, pulmonary administration routes are also considered.

The invention also relates to an implantable or transportable pump including a composition according to the invention.

The invention also relates to the use of a composition according to the invention which is intended to be placed in an implantable or transportable pump.

The invention also relates to single-dose formulations.

In an embodiment, the formulations are in the form of an injectable solution.

The preparation of a composition according to the invention has the advantage that it can be implemented by simple mixing of an aqueous solution of an amylin analog or of an amylin receptor agonist and of human insulin A21G, in aqueous solution or in lyophilized form.

If necessary, the composition of the mixture is adjusted in terms of excipients such as glycerol, m-cresol, zinc chloride and polysorbate 20 (Tween® 20). This addition can be carried out by addition of concentrated solutions of said excipients.

In an embodiment, the compositions are characterized in that said compositions have a solubility at a pH of 4.0 and a physical stability measured by ThT greater than that of a reference composition including an amylin analog or an amylin receptor agonist and a commercial prandial insulin.

The ThT is measured according to the protocol described in the examples.

In an embodiment, the compositions are characterized in that said compositions have a solubility at a pH of 4.0 and a physical stability measured by ThT greater than that of a reference composition including a GLP-1, a GLP-1 analog or a GLP-1 receptor agonist and a commercial prandial insulin.

The insulin and the insulin analogs can be obtained by methods of recombinant DNA technology using bacteria such as *Escherichia coli* and yeasts such as *Saccharomyces cerevisiae* (see, for example, G. Walsh Appl. Microbiol. Biotechnol. 2005, 67, 151-159). In general, a proinsulin is produced, which is then digested by enzymes such as trypsin and carboxypeptidase B to obtain the desired sequence.

For the production of human insulin A21G, the proinsulin is coded so that the glycine is in A21, and, after digestion by trypsin and carboxypeptidase B, the desired insulin is obtained. An operating procedure is described by Kohn et al., in Peptides 2007, 28, 935-948.

The invention also relates to the method for obtaining human insulin A21G, including at least one step consisting in reacting human insulin A21G, B31R, B32R (insulin glargine) with rat carboxypeptidase B at an insulin/carboxypeptidase ratio from 500 to 2000, at a pH from 7.5 to 8.5, and a temperature from 20 to 30° C. for 10 to 20 hours. The product can then be purified. This purification can be carried out by liquid chromatography.

The human insulin A21G can thus be obtained by removing the two arginines from insulin glargine by digestion with a carboxypeptidase B. After enzymatic digestion, the human insulin A21G is purified by chromatography and then isolated by lyophilization or by crystallization by conventional methods.

BRIEF DESCRIPTION OF THE FIGURES

FIG. 1 is a representation of the graphic determination of the fibrillation lag time based on a virtual example. On the abscissa, the time in minutes appears, and, on the ordinate, the fluorescence ThT appears in arbitrary units (a.u.), and LT stands for lag time.

The squares represent the concentration of insulin, and the triangles represent the concentration of pramlintide.

On the abscissa, the time in minutes after injection appears; on the ordinate on the left, the baseline-corrected insulin concentration in pmol/L appears, and, on the ordinate, the baseline-corrected pramlintide concentration in pmol/L appears.

Figure 3:
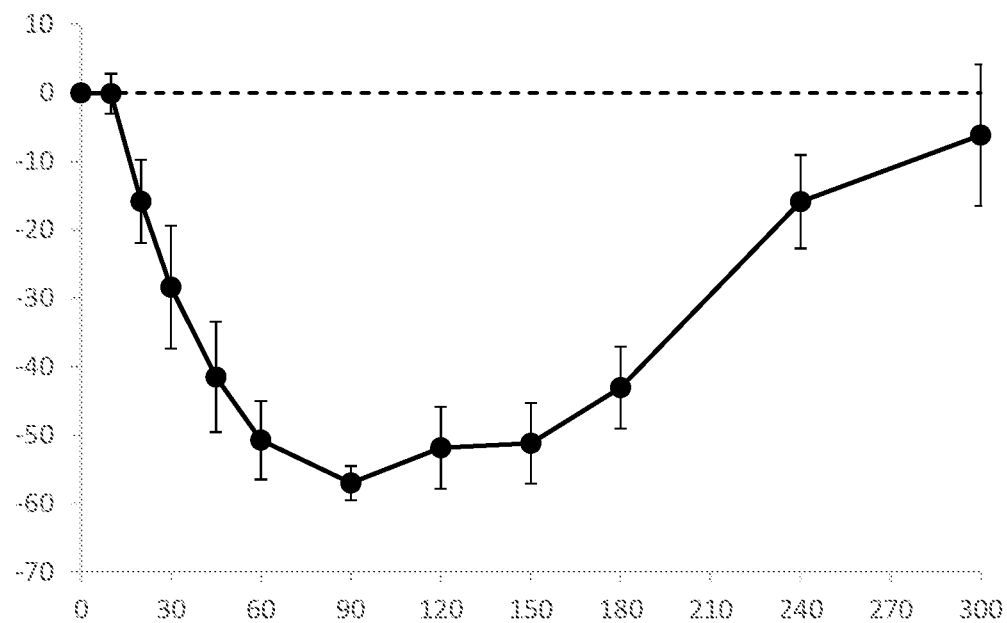

FIG. 3: Glycemia after administration of formulation A21-8 (mean±standard deviation).

On the abscissa, the time in minutes after injection appears, and, on the ordinate, the glycemia in % of the baseline level appears.

Figure 4:
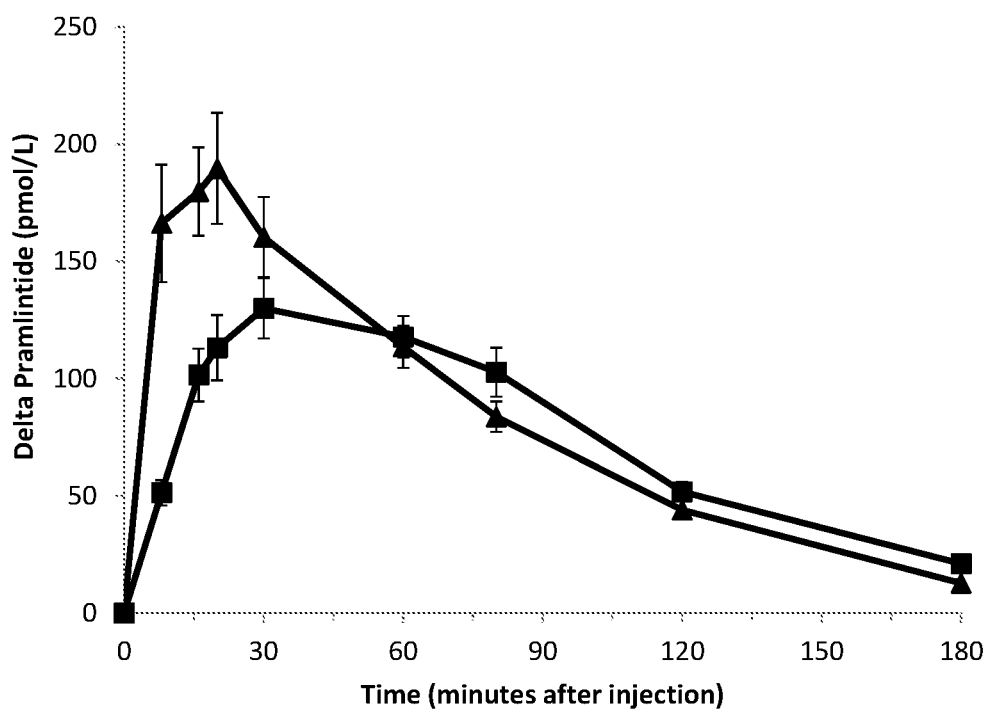

FIG. 4: Concentration of pramlintide after administration of formulation A21-9 (curve drawn with squares) and PRAM (curve drawn with triangles) (mean±standard deviation).

On the abscissa, the time in minutes after injection appears, and, on the ordinate, the baseline-corrected pramlintide concentrations appear (pre-dose concentrations subtracted individually), in pmol/L.

EXAMPLES

Example 1. Preparation of Human Insulin A21G 5 g of insulin glargine (Gan & Lee Pharmaceuticals) are mixed with the enzyme carboxypeptidase B (Reference 08039852001; Sigma-Aldrich) at pH 8.0 (pH adjusted by addition of Tris buffer), and the mixture is allowed to stand for 17 hours at 25° C., the insulin glargine concentration being approximately 4 mg/mL. The enzyme/glargine ratio is 1/500. The mixture is then purified by liquid chromatography, dialyzed against hydrochloric acid 0.01N and then lyophilized. The result is human insulin A21G with a purity of 98% and a yield of approximately 90%. The molecular weight of the insulin measured by mass spectrometry (Maldi-Tof) is 5752 Da. The human insulin A21G can also be obtained using the recombinant technology as described by Kohn et al. (Peptides 2007, 28, 935-948).

Example 2. Compositions of Prandial Insulins and of Pramlintide, Exenatide or Lixisenatide at Acidic pH Preparation of a Solution of Human Insulin A21G 100 U/mL (3.5 mg/mL) and of Pramlintide 1 mg/mL Containing m-Cresol (25 mM), Glycerol (184 mM) and Zinc Chloride (300 µM) at Acidic pH from of 3.5 or 4.0.

A concentrated solution of excipients (m-cresol, glycerol) is added to a concentrated solution of human insulin A21G (300 U/mL at pH 3.5). A concentrated solution of pramlintide (Ambiopharm) (10 mg/mL at pH 4) and a concentrated solution of zinc chloride are added to this concentrated solution of human insulin A21G and of excipients so as to obtain the intended final composition. The final pH, namely 3.5 or 4.0, is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin A21G 100 U/mL and of Pramlintide 0.6 mg/mL Containing m-Cresol (25 mM), Glycerol (184 mM) and Zinc Chloride (300 µM) at acidic pH of 4.0.

This solution is prepared in the same manner as the solution presented above.

Preparation of a Solution of Human Insulin A21G 100 U/mL and of Pramlintide 1 mg/mL Containing m-Cresol (25 mM) and Glycerol (184 mM) at Acidic pH of 4.0.

A concentrated solution of excipients (m-cresol, glycerol) is added to a concentrated solution of human insulin A21G (800 U/mL at pH 3.5). A concentrated solution of pramlintide (10 mg/mL at pH 4) is added to this concentrated solution of human insulin and of excipients so as to obtain the intended final composition. The final pH, namely 4.0, is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin A21G 100 U/mL and of Pramlintide 1 mg/mL Containing m-Cresol (25 mM), Glycerol (184 mM) and Tween 20 (10 µg/mL) at pH 4.

A concentrated solution of excipients (m-cresol, glycerol) is added to a concentrated solution of human insulin A21G (300 U/mL at pH 3.5). A concentrated solution of pramlintide (10 mg/mL at pH 4) and a concentrated solution of Tween 20 are added to this concentrated solution of human insulin A21G and of excipients so as to obtain the intended final composition. The final pH is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin A21G 100 U/mL and of Pramlintide 1 mg/mL Containing m-Cresol (25 mM), Glycerol (184 mM), Zinc Chloride (300 µM) and Tween 20 (10 µg/mL) at pH 4.

A concentrated solution of excipients (m-cresol, glycerol) is added to a concentrated solution of human insulin A21G (300 U/mL at pH 3.5). A concentrated solution of pramlintide (10 mg/mL at pH 4), a concentrated solution of zinc chloride and concentrated solution of Tween 20 are added to this concentrated solution of human insulin A21G and of excipients so as to obtain the intended final composition. The final pH is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin A21G 100 U/mL and of Exenatide 50 µg/mL Containing m-Cresol (25 mM), Glycerol (184 mM) and Zinc Chloride (300 µM) at Acidic pH.

A concentrated solution of excipients (m-cresol, glycerol) is added to a concentrated solution of human insulin A21G (300 U/mL at pH 3.5). A concentrated solution of exenatide (Bachem) (10.5 mg/mL at pH 4) and a concentrated solution of zinc chloride are added to this concentrated solution of human insulin A21G and of excipients so as to obtain the intended final composition. The final pH 4.0 is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin A21G 100 U/mL and of Lixisenatide 100 µg/mL Containing m-Cresol (25 mM), Glycerol (184 mM) and Zinc Chloride (300 µM) at Acidic pH.

A concentrated solution of excipients (m-cresol, glycerol) is added to a concentrated solution of human insulin A21G (230 U/mL at pH 3.5). A concentrated solution of lixisenatide (Ambiopharm) (10.5 mg/mL at pH 4) and a concentrated solution of zinc chloride are added to this concentrated solution of human insulin A21G and of excipients so as to obtain the intended final composition. The final pH 4.0 is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin A21G 100 U/mL, of Exenatide 50 µg/mL and of Pramlintide 0.6 mg/mL Containing m-Cresol (25 mM), Glycerol (184 mM) and Tween 20 (10 µg/mL) at Acidic pH of 4.0.

A concentrated solution of excipients (m-cresol, glycerol) is added to a concentrated solution of human insulin A21G (300 U/mL at pH 3.5). A concentrated solution of pramlintide (Ambiopharm) (10 mg/mL at pH 4), a concentrated solution of exenatide (Bachem) (10.5 mg/mL at pH 4) and a concentrated solution of Tween 20 are added to this concentrated solution of human insulin A21G and of excipients so as to obtain the intended final composition. The final pH 4.0 is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Human Insulin 100 U/mL and of Pramlintide 1 Mg/mL Containing m-Cresol (25 mM), Glycerol (184 mM) and Zinc Chloride (300 µM) at Acidic pH of 3.5 or 4.0.

A concentrated solution of excipients (m-cresol, glycerol) is added to a concentrated solution of human insulin (Amphastar Pharmaceuticals) (800 U/mL at pH 3.5). A concentrated solution of pramlintide (10 mg/mL at pH 4) and a concentrated solution of zinc chloride are added to this concentrated solution of human insulin and of excipients so as to obtain the intended final composition. The final pH, namely 3.5 or 4.0, is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Insulin Aspart 100 U/mL and of Pramlintide 1 Mg/mL Containing m-Cresol (25 mM), Glycerol (184 mM) and Zinc Chloride (300 µM) at Acidic pH of 3.5 or 4.0.

A concentrated solution of excipients (m-cresol, glycerol) is added to a concentrated solution of insulin aspart (HEC Pharmaceuticals) (500 U/mL at pH 3). A concentrated solution of pramlintide (10 mg/mL at pH 4) and a concentrated solution of zinc chloride are added to this concentrated solution of insulin aspart and of excipients so as to obtain the intended final composition. The final pH, namely 3.5 or 4.0, is adjusted to the desired value by addition of an aqueous solution of NaOH or of HCl. The solution adjusted to pH 4.0 is turbid after the pH adjustment. The solution adjusted to pH 3.5 is clear. It is subjected to a 0.22 µm filtration and stored in glass cartridges (1 mL of solution per cartridge).

Preparation of a Solution of Insulin Lispro 100 U/mL and of Pramlintide 1 Mg/mL Containing m-Cresol (25 mM), Glycerol (184 mM) and Zinc Chloride (300 µM) at Acidic pH of 3.5 or 4.0.

A concentrated solution of excipients (m-cresol, glycerol) is added to a concentrated solution of insulin lispro (Gan & Lee Pharmaceuticals) (650 U/mL at pH 3). A concentrated solution of pramlintide (10 mg/mL at pH 4) and a concentrated solution of zinc chloride are added to this concentrated solution of insulin lispro and of excipients so as to obtain the intended final composition. The final pH, namely 3.5 or 4.0, is adjusted to the desired value by addition of an aqueous solution of NaOH or of HCl. The solution obtained is clear and homogeneous; it is subjected to a 0.22 µm filtration and stored in glass cartridges (1 mL of solution per cartridge).

Preparation of a Solution of Insulin Glulisine 100 U/mL and of Pramlintide 1 Mg/mL Containing the Excipients of the Commercial Product Apidra® (29 mM of m-Cresol, 50 mM of Tris, 86 mM of Zinc Chloride and 8.15 µM of Tween 20) at Acidic pH of 3.0, 3.5 or 4.0.

The pH of the commercial solution of insulin glulisine, Apidra, is adjusted to pH 2.5 by addition of an aqueous solution of HCl. This solution is added to pramlintide in the form of a powder so as to obtain a solution containing 100 U/mL of insulin and 1 mg/mL of pramlintide. The final pH is adjusted to the desired value by addition of an aqueous solution of NaOH or of HCl. The solutions adjusted to pH 3.5 and 4.0 are turbid after the pH adjustment. The solution adjusted to pH 3.0 is clear. It is subjected to a 0.22 µm filtration and stored in glass cartridges (1 mL of solution per cartridge). After a few hours of storage, the solution is turbid and heterogeneous.

Preparation of a Solution of Pramlintide 1 mg/mL Containing m-Cresol (20 mM), Mannitol (236 mM) and Acetic Acid/Sodium Acetate Buffer (30 mM) at pH 4.0.

A concentrated solution of pramlintide at 10 mg/mL is prepared by dissolution of pramlintide in the form of a powder purchased from Ambiopharm. This solution is added to a concentrated solution of excipients (m-cresol, mannitol, acetic acid/sodium acetate buffer) so as to obtain the intended final composition. The final pH is adjusted to 4.0±0.2 by addition of NaOH/HCl.

Preparation of a Solution of Human Insulin A21G 100 U/mL and of Pramlintide 0.6 mg/mL Containing m-Cresol (25 mM), Glycerol (184 mM), Acetic Acid/Sodium Acetate Buffer (18 mM) and Tween 20 (8 µM) at pH 4.

Concentrated solutions of glycerol and m-cresol are added to a concentrated solution of human insulin A21G in an acetic acid/sodium acetate buffer at pH 4 (300 U/mL at pH 4). A concentrated solution of pramlintide (Ambiopharm) (10 mg/mL at pH 4) and a concentrated solution of Tween 20 are finally added to this concentrated solution of human insulin A21G and of excipients so as to obtain the intended final composition. The final pH is adjusted to the desired value by addition of an aqueous solution of NaOH or of HCl. The solution obtained is clear and homogeneous; it is subjected to a 0.22 µm filtration.

The compositions prepared above are presented in table 1 below:

TABLE 1

Compositions of insulin and/or of glucagon suppressors

| Compositions | Insulin type (U/mL) | Pramlintide (mg/mL) | pH | Zinc (µM) | Tween 20 (µg/mL) | GLP-1 RA | Other excipients |
|---|---|---|---|---|---|---|---|
| A21-1 | Human insulin A21G (100) | 1.0 | 4.0 | 300 | 0 | 0 | m-cresol (25 mM) glycerol (184 mM) |
| A21-2 | Human insulin A21G (100) | 1.0 | 4.0 | 0 | 0 | 0 | m-cresol (25 mM) glycerol (184 mM) |
| A21-3 | Human insulin A21G (100) | 1.0 | 3.5 | 300 | 0 | 0 | m-cresol (25 mM) glycerol (184 mM) |
| A21-4 | Human insulin A21G (100) | 1.0 | 4.0 | 0 | 10 | 0 | m-cresol (25 mM) glycerol (184 mM) |
| A21-5 | Human insulin A21G (100) | 1.0 | 4.0 | 300 | 10 | 0 | m-cresol (25 mM) glycerol (184 mM) |
| A21-6 | Human insulin A21G (100) | 0 | 4.0 | 300 | 0 | exenatide 50 µg/mL | m-cresol (25 mM) glycerol (184 mM) |
| A21-7 | Human insulin A21G (100) | 0 | 4.0 | 300 | 0 | lixisenatide 100 µg/mL | m-cresol (25 mM) glycerol (184 mM) |
| A21-8 | Human insulin A21G (100) | 0.6 | 4.0 | 300 | 0 | 0 | m-cresol (25 mM) glycerol (184 mM) |
| RHI-1 | Human insulin (100) | 1.0 | 4.0 | 300 | 0 | 0 | m-cresol (25 mM) glycerol (184 mM) |
| RHI-2 | Human insulin (100) | 1.0 | 3.5 | 300 | 0 | 0 | m-cresol (25 mM) glycerol (184 mM) |
| ASP-1 | Insulin aspart (100) | 1.0 | 4.0 | 300 | 0 | 0 | m-cresol (25 mM) glycerol (184 mM) |

TABLE 1-continued

Compositions of insulin and/or of glucagon suppressors

| Compositions | Insulin type (U/mL) | Pramlintide (mg/mL) | pH | Zinc (µM) | Tween 20 (µg/mL) | GLP-1 RA | Other excipients |
|---|---|---|---|---|---|---|---|
| ASP-2 | Insulin aspart (100) | 1.0 | 3.5 | 300 | 0 | 0 | m-cresol (25 mM) glycerol (184 mM) |
| GLU-1 | Insulin glulisine (100) | 1.0 | 4.0 | 300 | 10 | 0 | m-cresol (29 mM) Tris (50 mM) NaCl (86 mM) |
| GLU-2 | Insulin glulisine (100) | 1.0 | 3.5 | | 10 | 0 | m-cresol (29 mM Tris (50 mM) NaCl (86 mM) |
| GLU-3 | Insulin glulisine (100) | 1.0 | 3.0 | | 10 | 0 | m-cresol (29 mM) Tris (50 mM) NaCl (86 mM) |
| LIS-1 | Insulin lispro (100) | 1.0 | 4.0 | 300 | 0 | 0 | m-cresol (25 mM) glycerol (184 mM) |
| LIS-2 | Insulin lispro (100) | 1.0 | 3.5 | 300 | 0 | 0 | m-cresol (25 mM) glycerol (184 mM) |
| PRAM | — | 1.0 | 4.0 | — | — | 0 | m-cresol (20 mM) mannitol (236 mM) acetate (30 mM) |
| A21-9 | Human insulin A21G (100) | 0.6 | 4.0 | — | 10 | 0 | m-cresol (25 mM) glycerol (184 mM) acetate (18 mM) |
| A21-10 | Human insulin A21G (100) | 0.6 | 4.0 | — | 10 | exenatide 50 µg/mL | m-cresol (25 mM) glycerol (184 mM) |

Example 3. Study of the Compatibility of the Prandial Insulins with Pramlintide at Acidic pH Visual Appearance of the Solutions of Insulin and of Pramlintide at Acidic pH.

The observation is carried out at ambient temperature after 2 to 3 hours of stabilization of the solution stored in cartridges. Table 2 presents the visual appearance of solutions of insulin and of pramlintide described above.

TABLE 2

Visual appearance of the solutions of insulin and of pramlintide.

| Composition | Visual appearance |
|---|---|
| A21-1 | Clear |
| A21-2 | Clear |
| A21-3 | Clear |
| RHI-1 | Clear |
| RHI-2 | Clear |
| ASP-1 | Turbid |
| ASP-2 | Clear |
| GLU-1 | Turbid |
| GLU-2 | Turbid |
| GLU-3 | Turbid |
| LIS-1 | Clear |
| LIS-2 | Clear |

Among the insulins evaluated, only human insulin, insulin lispro and human insulin A21G enable to obtain a homogeneous and clear formulation with pramlintide at pH 4, demonstrating the solubility of the species. The insulins aspart and glulisine are not suitable for obtaining a clear formulation with pramlintide at pH 4.0.

Example 4. Study of the Fibrillation Lag Time

Principle

The poor stability of a peptide can lead to the formation of amyloid fibrils which are defined as ordered macromolecular structures. These fibrils may lead to the formation of a gel within the sample.

The test of monitoring the fluorescence of thioflavin T (ThT) is used to analyze the physical stability of the formulations. Thioflavin T is a small probe molecule which has a characteristic fluorescence signature when it binds to amyloid fibrils (Naiki et al. (1989) Anal. BioChem. 177, 244-249; LeVine (1999) Methods. Enzymol. 309, 274-284).

This method enables to monitor the formation of fibrils at low ThT concentrations within undiluted formulations. This monitoring is carried out under accelerated stability conditions: under stirring and at 37° C.

Experimental Conditions

The samples were prepared immediately before the start of the measurement. The preparation of each composition is described in the associated example. Thioflavin T is added to the composition from a concentrated stock solution so as to induce a negligible dilution of the composition. The thioflavin T concentration in the composition is 40 µM. A volume of 150 µL of the composition was introduced into a well of a 96-well plate. Each composition was analyzed in triplicate within the same plate. The plate was sealed with transparent film to prevent evaporation of the composition.

This plate was then placed in the enclosure of a plate reader (EnVision 2104 Multilabel, Perkin Elmer). The temperature is set at 37° C., and a lateral agitation at 960 rpm with an amplitude of 1 mm is imposed.

A reading of the fluorescence intensity in each well versus time is carried out with an excitation wavelength of 442 nm and an emission wavelength of 482 nm.

The fibrillation process manifests itself by a strong increase in fluorescence after a delay referred to as lag time.

Figure 1:
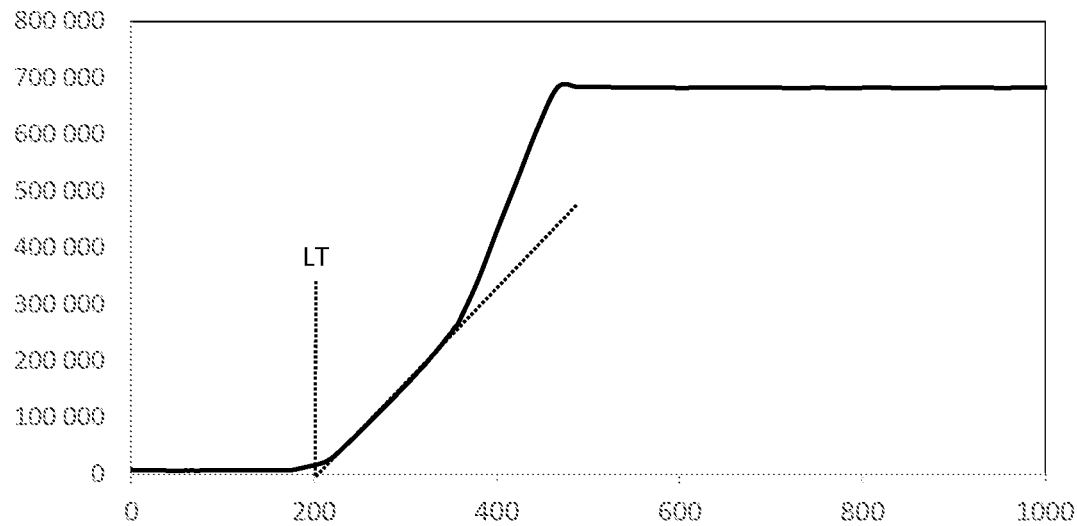
FIG. 1: Graphic determination of the fibrillation lag time.

For each well, this delay is determined graphically as the intersection between the baseline of the fluorescence signal and the slope of the fluorescence curve versus time, which is determined during the initial strong increase in fluorescence, as shown in FIG. 1. The value of the lag time plotted corresponds to the average of the lag times of 3 wells.

The clear solutions of pramlintide and insulin at pH 3.5 and 4.0 of the preceding example are then subjected to the fibrillation test in the presence of ThT.

The lag time reported in Table 3 corresponds to the average of 3 measurements; the uncertainty interval corresponds to the standard deviation between these 3 results.

TABLE 3

Lag times of the solutions of insulin and pramlintide.

| Composition | Lag time (h) |
|---|---|
| A21-1 | 13.7 +/− 0.8 |
| A21-2 | 10.4 +/− 1.8 |
| A21-3 | 15.6 +/− 5.3 |
| RHI-1 | 5.0 +/− 0.7 |
| RHI-2 | 1.7 +/− 0 |
| ASP-2 | 2.0 +/− 0 |
| LIS-1 | 1.8 +/− 0.1 |
| LIS-2 | 4.3 +/− 0.4 |

Unexpectedly, the formulations containing human insulin A21G have fibrillation lag times that are much longer than those of the commercial insulins tested at pH 3.5 or at pH 4.0, in particular longer than the rapid insulin analogs, insulin lispro and insulin aspart.

Example 5. Study of the Fibrillation Lag Time in the Presence of Tween 20

In Table 4, the lag times of solutions of human insulin A21G and pramlintide at pH 4 in the presence of Tween 20 are presented.

TABLE 4

Lag time of the solutions of human insulin A21G and pramlintide in the presence of Tween 20.

| Composition | Lag time (h) |
|---|---|
| A21-4 | 38.1 +/− 8.8 |
| A21-5 | 48.3 +/− 9.2 |

The physical stability is thus improved in the presence of Tween 20 at 10 µg/mL

Example 6. Physical Stability of the Formulations at 30° C. Under Static Conditions Glass cartridges filled with 1 mL of composition are placed in an oven maintained at 30° C. These cartridges are inspected visually in order to detect the appearance of visible particles or of turbidity. This inspection is carried out according to the recommendations of the European Pharmacopoeia (EP 2.9.20): the cartridges are subjected to an illumination of at least 2000 lux and are observed on a white background and on a black background. These results are in agreement with the US pharmacopoeia (USP <790>).

TABLE 5

Physical stability of the solutions of insulin and pramlintide at 30° C. under static conditions.

| Composition | Visual appearance after 4 weeks |
|---|---|
| A21-4 | Clear |
| A21-5 | Clear |
| A21-2 | Clear |
| A21-1 | Clear |
| A21-3 | Clear |
| ASP-2 | Turbid |

Insulin aspart formulated with pramlintide at pH 3.5 is less stable than human insulin A21G formulated with pramlintide at pH 3.5 or 4.0.

Example 7. Study of the Physical Stability of Human Insulin A21G with Exenatide and Lixisenatide Formulations A21-6 and A21-7 are placed in cartridges and then kept at 30° C. for 4 weeks. The fibrillation lag times are measured for extemporaneously prepared formulations and presented in table 6.

TABLE 6

Lag time and physical stability at 30° C. under static conditions of the solutions of human insulin A21G and exenatide or lixisenatide.

| Composition | Lag time (h) | Visual appearance after 4 weeks at 30° C. |
|---|---|---|
| A21-6 | 18.1 +/− 5.6 | Clear |
| A21-7 | 33.0 +/− 9.7 | Clear |

Example 8. Chemical Stability of a Formulation of Human Insulin A21G and Pramlintide All the formulations are at pH 4.0 or pH 3.5 and contain 100 U/mL of human insulin A21G, 1 mg/mL of pramlintide, 25 mM of m-cresol and 184 mM of glycerol. The formulations are stored in glass cartridges and kept at 30° C. under static conditions. Human insulin A21G and pramlintide are assayed by reverse phase liquid chromatography (HPLC). The measurements are presented in table 7.

TABLE 7

Change of the concentrations of insulin (a) in U/mL and of pramlintide (b) in mg/mL

| Composition | Concentration at the initial time | | Concentration after 4 weeks | |
|---|---|---|---|---|
| | (a) | (b) | (a) | (b) |
| A21-1 | 105 | 1.05 | 103 | 1.02 |
| A21-2 | 105 | 1.02 | 106 | 1.03 |
| A21-3 | 101 | 1.12 | 105 | 1.03 |
| RHI-1 | 101 | 1.6 | 76 | 1.03 |
| RHI-2 | 99 | 1.02 | 62 | 1.03 |
| LIS-1 | 105 | 1.07 | 89 | 1.03 |
| LIS-2 | 106 | 1.05 | 82 | 1.04 |
| ASP-2 | 104 | 1.05 | 55 | 1.02 |

The formulations containing human insulin A21G and pramlintide exhibit good chemical stability after 4 weeks at 30° C. The formulations of pramlintide with commercial insulins undergo rapid degradation at pH 4.0 and even more rapid degradation at pH 3.5.

Example 9. Pharmacokinetic and Pharmacodynamic Studies in Dogs

Pharmacokinetic and pharmacodynamic study in dogs of the composition consisting of human insulin A21G (100 U/mL, that is to say 3.5 mg/mL) and pramlintide (0.6 mg/mL). The tested formulation is at pH 4.0 and contains 25 mM of m-cresol and 184 mM of glycerol (Formulation A21-8).

Four animals which had fasted for approximately 18 hours received injections by subcutaneous administration in the neck at the dose of 0.2 U/kg of insulin and 0.12 µg/kg of pramlintide. In the hour preceding the injection, one or more blood samples are drawn in order to determine the basal level of glucose, of insulin and of pramlintide. Blood samples are then drawn during the 5 hours after administration of the formulation. The glycemia is determined by means of a glucometer. The levels of insulin and of pramlintide in the plasma are determined by an ELISA test.

The pharmacokinetic parameters of formulation A21-8 are estimated based on baseline-corrected insulin and pramlintide concentrations in the plasma. A standard non-compartmental analysis is carried out with the aid of the software Phoenix WinNonlin (version 7, Certara). The values of the parameters (mean±standard deviation) are reported in tables 8 and 9 below:

TABLE 8

PK parameters of total insulin analog

| Formulation | Tmax insulin (min) | Cmax insulin (pmol/L) | AUC0-last insulin (min*pmol/L) |
|---|---|---|---|
| A21-8 | 38 ± 26 | 218 ± 141 | 16165 ± 4160 |

TABLE 9

PK parameters of pramlintide

| Formulation | Tmax pramlintide (min) | Cmax pramlintide (pmol/L) | AUC0O-last pramlintide (min*pmol/L) |
|---|---|---|---|
| A21-8 | 20 ± 8 | 104 ± 39 | 5121 ± 2961 |

Figure 2:
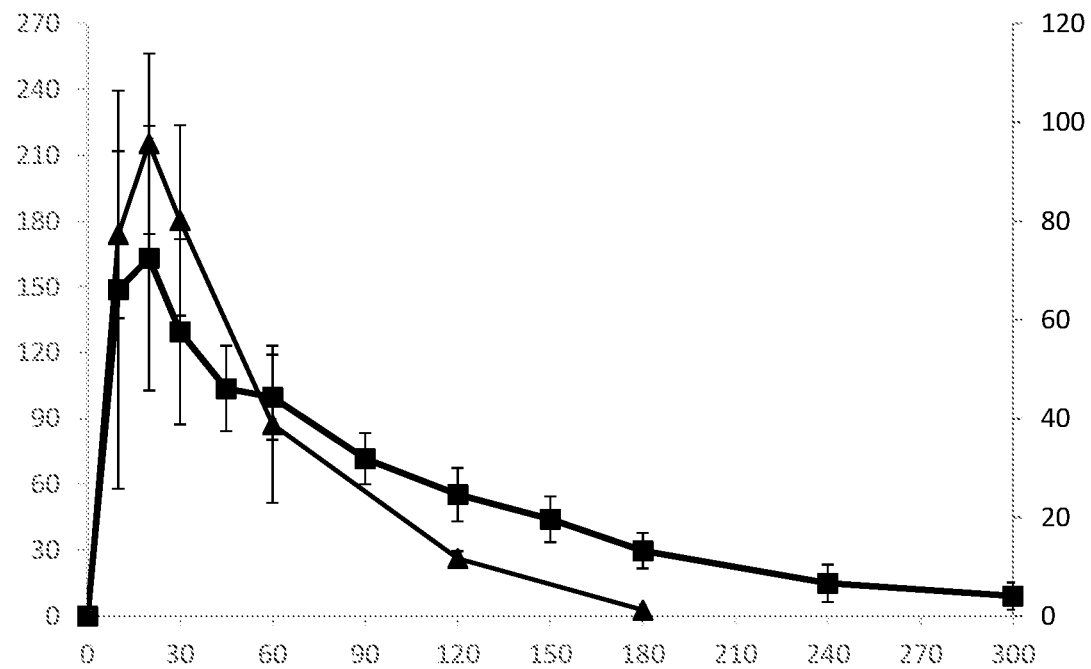
FIG. 2: Concentrations of pramlintide and insulin in the plasma after administration of formulation A21-8 (mean±standard deviation).

The mean pharmacokinetic (PK) profiles of total insulin (squares) and of pramlintide (triangles) in the plasma are presented in FIG. 2.

The mean glycemia profiles expressed as percentages of the baseline level are represented in FIG. 3.

It is observed that pramlintide and human insulin A21G both have prandial absorption kinetics giving rise to an early hypoglycemic activity followed by a return to a level close to baseline glycemia after 5 hours post-administration. These pharmacokinetic and pharmacodynamic results clearly indicate that Formulation A21-8 is compatible with use at meal time.

Example 10: Pharmacokinetic Studies of Pramlintide in Pigs

Pharmacokinetic study in pigs of the composition consisting of human insulin A21G (3.5 mg/mL equivalent to 100 U/mL of insulin) and pramlintide (0.6 mg/mL).

Domestic pigs weighing approximately 50 kg, catheterized beforehand in the jugular, were fasted for 2.5 hours before the start of the experiment. During the hour preceding the injection of insulin, 3 blood samples were drawn to determine the baseline level of glucose and of insulin.

The injection of the formulations of human insulin A21G combined with pramlintide (A21-9) or of pramlintide (PRAM) at the dose of 0.2 U of insulin/kg and 1.2 µg of pramlintide/kg is performed subcutaneously in the flank of the animal with the aid of an insulin pen (Novo, Sanofi or Eli Lilly) equipped with a 31 G needle.

In order to determine the concentrations of pramlintide in the plasma, blood samples are drawn at the following times: 4, 8, 12, 16, 20, 30, 40, 50, 60, 70, 80, 100, 120, 150 and 180 minutes. After each drawing, the catheter is rinsed with a dilute heparin solution.

Pharmacokinetic Results of the Solution of Human Insulin A21G and Pramlintide A21-9 and of the Solution of Pramlintide PRAM in Pigs The results of 3 studies carried out on the same cohort of pigs are pooled to compare the pharmacokinetics of pramlintide between formulation A21-9 and formulation PRAM. The pharmacokinetic parameters of formulations A21-9 and PRAM are estimated based on the baseline-corrected pramlintide concentrations in the plasma. A standard non-compartmental analysis is carried out with the aid of the software Phoenix WinNonlin (version 7, Certara). The values of the parameters (mean±standard deviation) are plotted in the following table.

TABLE 10

PK parameters of pramlintide of compositions A21-9 and PRAM

| Formulation | Peptides (mg/mL) | N | $t_{max}$ pramlintide (min) | $AUC_{0-30\ min}$ pramlintide (min*pmol/L) | $AUC_{0-t}$ pramlintide (min*pmol/L) |
|---|---|---|---|---|---|
| A21-9 | human insulin A21G (3.5) pramlintide (0.6) | 34 | 42.1 ± 22.4 | 2461 ± 1467 | 13642 ± 5934 |
| PRAM | Pramlintide (0.6) | 34 | 23.2 ± 15.0 | 4357 ± 3127 | 14806 ± 7872 |
| Value p (significant if p < 0.05) | Comparison A21-9 versus PRAM | 34 | 0.0004 | 0.0007 | 0.8018 |

Where $t_{max}$=time necessary to observe the maximum plasma concentration; $AUC_{0-30\ min}$=area under the curve of the plasma concentration versus time between 0 and 30 min after injection; $AUC_{0-t}$=area under the curve of the plasma concentrations versus time between 0 and the last quantifiable concentration after injection The pharmacokinetic results of pramlintide obtained with formulations A21-9 and PRAM are presented in FIG. 4. The analysis of these profiles and of the parameters indicates that the combination of human insulin A21G and of pramlintide (formulation A21-9, curve plotted with squares) leads a significant slowing of the absorption of pramlintide compared to pramlintide alone (formulation PRAM, curve plotted with triangles). Formulation A21-9 leads to a plasma peak ($t_{max}$) which is significantly delayed (approximately 18 min, $p<0.05$) and to an early plasma exposure to pramlintide ($AUC_{0-30\ min}$) which is significantly decreased (approximately 43%, $p<0.05$) in comparison to formulation PRAM. On the other hand, the total plasma exposure to pramlintide ($AUC_{0-t}$) appears to be similar between the two formulations, suggesting comparable bioavailabilities.

Example 11. Study of Food Consumption in Rats after Injection of Control Compositions and after Injection of Compositions Including Human Insulin A21G and/or Pramlintide This study was carried out on a population of 40 at least 6 week old male Sprague Dawley rats.

The rats had free access to food and water, except for a 6 hour fasting period preceding the subcutaneous injection of the compositions described in the table below.

TABLE 11

Compositions injected in the rats and number of rats treated

| Composition | Control | Humulin ® | PRAM | A21-9 |
|---|---|---|---|---|
| [Pramlintide] (mg/mL) | — | — | 1 | 0.6 |
| Dose of Pramlintide (µg/kg) | — | — | 60 | 60 |
| Insulin type | — | Human | — | Human A21G |
| [Insulin] (U/mL) | | 100 | | 100 |
| Insulin dose (U/kg) | — | 10 | — | 10 |
| Number of rats | 10 | 10 | 10 | 10 |

The control composition is a saline solution, that is to say an aqueous solution containing 150 mM of NaCl.

The composition Humulin® R is a commercial solution of human insulin marketed by ELI LILLY. This product is a human insulin at 100 U/mL. The excipients of Humulin® R are glycerol, meta-cresol, sodium hydroxide and hydrochloric acid for pH adjustment (pH 7.0-7.8) and water.

At t0, immediately after the injection, the food is distributed (approximately 100 g par rat). The food consumption (cumulative mean) is measured one, two and three hours after t0, or t+1 h, t+2 h and t+3 h.

The results are presented in the following table:

TABLE 12 food consumption 1, 2 and 3 hours after injection

| Compositions | Control | Humulin | PRAM | A21-9 |
|---|---|---|---|---|
| Food consumption at t + 1 h (g) | 3.8 | 4.7 | 1.5 | 3.2 |
| Food consumption at t + 2 h (g) | 4.4 | 5.3 | 3.3 | 4.4 |
| Food consumption at t + 3 h (g) | 5.9 | 6.9 | 4.2 | 5.3 |

These results show that the composition A21-9 combining insulin A21G and pramlintide enables not only to decrease the food consumption induced by the injection of insulin, but also to limit the food consumption to a level less than or equal to the level of the control group that received an injection of Control composition (saline solution).

The invention claimed is:

1. A composition in the form of an injectable aqueous solution, the pH of which is from 3.5 to 4.4, comprising at least human insulin A21G referred to as regular and at least one glucagon suppressor with prandial action.

2. The composition according to claim 1, wherein the glucagon suppressor with prandial action is an amylin analog or an amylin receptor agonist or a GLP-1 analog or a GLP-1 receptor agonist (GLP-1 RA).

3. The composition according to claim 1, wherein the glucagon suppressor with prandial action is an amylin analog or an amylin receptor agonist.

4. The composition according to claim 1, wherein the glucagon suppressor with prandial action is pramlintide.

5. The composition according to claim 1, wherein the glucagon suppressor with prandial action is exenatide.

6. The composition according to claim 1, wherein the glucagon suppressor with prandial action is lixisenatide.

7. The composition according to claim 1, wherein the concentration of human insulin A21G is from 2 to 20 mg/mL.

8. The composition according to claim 1, wherein the concentration of human insulin A21G is 3.5 mg/mL.

9. The composition according to claim 1, wherein the concentration of glucagon suppressor with prandial action is from 0.01 to 10 mg/mL.

10. The composition according to claim 1, wherein the pH of the solution is from 3.8 to 4.2.

11. The composition according to claim 1, wherein the pH of the solution is 4.0.

12. The composition according to claim 1, wherein the composition further comprises a zinc salt.

13. The composition according to claim 1, wherein the composition further comprises m-cresol.

14. The composition according to claim 1, wherein the composition further comprises a polysorbate 20.

15. The composition according to claim 1, wherein the composition further comprises a poloxamer 188 excipient.

16. The composition according to claim 1, wherein the composition further comprises methionine.

17. The composition according to claim 1, as part of a diabetes treatment method, wherein the composition is administered in a bolus before meals.

18. The composition according to claim 1, as part of a diabetes treatment method, wherein the composition is administered to improve control of postprandial glycemia.

19. The composition according to claim 1, as part of a diabetes treatment method, wherein the composition is administered to improve control of postprandial glycemia and to decrease the adverse effects of pramlintide.

20. The composition according to claim 1, as part of a diabetes treatment method, wherein the composition enables a decrease in food consumption induced by insulin.

* * * * *